(12) United States Patent
Mueller (10) Patent No.: US 9,375,205 B2
(45) Date of Patent: Jun. 28, 2016

(54) DEPLOYMENT MECHANISMS FOR SURGICAL INSTRUMENTS

(71) Applicant: COVIDIEN LP, Mansfield, MA (US)

(72) Inventor: Peter M. Mueller, Frederick, CO (US)

(73) Assignee: COVIDIEN LP, Mansfield, MA (US)

( * ) Notice: Subject to any disclaimer, the term of this patent is extended or adjusted under 35 U.S.C. 154(b) by 389 days.

(21) Appl. No.: 14/047,474

(22) Filed: Oct. 7, 2013

(65) Prior Publication Data

US 2014/0135758 A1 May 15, 2014

Related U.S. Application Data

(60) Provisional application No. 61/726,988, filed on Nov. 15, 2012.

(51) Int. Cl.
| | |
|---|---|
| *A61B 18/08* | (2006.01) |
| *A61B 17/00* | (2006.01) |
| *A61B 18/14* | (2006.01) |
| *A61B 18/00* | (2006.01) |

(52) U.S. Cl.
CPC ....... *A61B 17/00234* (2013.01); *A61B 18/1445* (2013.01); *A61B 2018/0063* (2013.01); *A61B 2018/00083* (2013.01); *A61B 2018/00601* (2013.01); *A61B 2018/1455* (2013.01)

(58) Field of Classification Search
CPC .............. A61B 2017/2919; A61B 2017/2916; A61B 2017/2936; A61B 2017/2939; A61B 18/1442

See application file for complete search history.

(56) References Cited

U.S. PATENT DOCUMENTS

| | | |
|---|---|---|
| 4,005,714 A | 2/1977 | Hiltebrandt |
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 5,026,379 A | 6/1991 | Yoon |
| D343,453 S | 1/1994 | Noda |
| D348,930 S | 7/1994 | Olson |

(Continued)

FOREIGN PATENT DOCUMENTS

| | | |
|---|---|---|
| AU | 2011253698 A1 | 12/2011 |
| CN | 201299462 | 9/2009 |

(Continued)

OTHER PUBLICATIONS

European Search Report EP13174297 dated Nov. 7, 2013.

(Continued)

*Primary Examiner* — Jocelyn D Ram (57) ABSTRACT

A surgical instrument includes a first drive assembly, a second drive assembly, and a deployment mechanism. The first drive assembly is coupled to a first component and is configured to translate a first longitudinal distance X1 to deploy the first component. The second drive assembly is coupled to a second component and is configured to translate a second longitudinal distance X2 to deploy the second component. The deployment mechanism is operably coupled to both the first and second drive assemblies and is configured to move from a first position to a second position to translate the first and second drive assemblies the respective first and second longitudinal distances X1 and X2 to deploy the first and second components.

19 Claims, 6 Drawing Sheets

(56) References Cited

U.S. PATENT DOCUMENTS

| | | | |
|---|---|---|---|
| D349,341 S | 8/1994 | Lichtman et al. | |
| 5,342,359 A | 8/1994 | Rydell | |
| D354,564 S | 1/1995 | Medema | |
| D358,887 S | 5/1995 | Feinberg | |
| 5,611,813 A | 3/1997 | Lichtman | |
| D384,413 S | 9/1997 | Zlock et al. | |
| H1745 H | 8/1998 | Paraschac | |
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| 6,558,385 B1 | 5/2003 | McClurken et al. | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| 7,208,005 B2 * | 4/2007 | Frecker | A61B 17/29 606/167 |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| 7,445,621 B2 | 11/2008 | Dumbauld et al. | |
| D582,038 S | 12/2008 | Swoyer et al. | |
| 7,481,810 B2 | 1/2009 | Dumbauld et al. | |
| 7,628,791 B2 * | 12/2009 | Garrison | A61B 18/1445 606/171 |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| 7,771,425 B2 * | 8/2010 | Dycus | A61B 18/1445 606/41 |
| 7,789,878 B2 | 9/2010 | Dumbauld et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, IV et al. | |
| D661,394 S | 6/2012 | Romero et al. | |
| 8,342,379 B2 * | 1/2013 | Whitman | A61B 17/07207 227/178.1 |
| 8,490,713 B2 * | 7/2013 | Furnish | A61B 17/0469 173/18 |
| 8,672,939 B2 * | 3/2014 | Garrison | A61B 18/1445 606/51 |
| 8,702,749 B2 * | 4/2014 | Twomey | A61B 18/1445 606/205 |
| 9,161,807 B2 * | 10/2015 | Garrison | A61B 17/29 |
| 2002/0072766 A1 * | 6/2002 | Hunt | A61B 17/29 606/205 |
| 2005/0113827 A1 * | 5/2005 | Dumbauld | A61B 18/1445 606/45 |
| 2006/0129146 A1 | 6/2006 | Dycus et al. | |
| 2007/0278277 A1 | 12/2007 | Wixey et al. | |
| 2008/0083813 A1 | 4/2008 | Zemlok et al. | |
| 2009/0012556 A1 | 1/2009 | Boudreaux et al. | |
| 2009/0112206 A1 | 4/2009 | Dumbauld et al. | |
| 2009/0171350 A1 | 7/2009 | Dycus et al. | |
| 2009/0182327 A1 | 7/2009 | Unger | |
| 2010/0292690 A1 | 11/2010 | Livneh | |
| 2011/0087218 A1 * | 4/2011 | Boudreaux | A61B 18/1445 606/41 |
| 2011/0276049 A1 | 11/2011 | Gerhardt | |
| 2011/0319886 A1 | 12/2011 | Chojin et al. | |
| 2012/0083827 A1 | 4/2012 | Artale et al. | |
| 2012/0209263 A1 | 8/2012 | Sharp et al. | |
| 2013/0218198 A1 | 8/2013 | Larson et al. | |
| 2014/0025052 A1 * | 1/2014 | Nau, Jr. | A61B 18/1445 606/13 |

FOREIGN PATENT DOCUMENTS

| | | |
|---|---|---|
| DE | 2415263 A1 | 10/1975 |
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 4242143 A1 | 6/1994 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| EP | 1530952 A1 | 5/2005 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |

(56) References Cited

FOREIGN PATENT DOCUMENTS

| | | |
|---|---|---|
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2006-015078 A | 1/2006 |
| JP | 2006-501939 A | 1/2006 |
| JP | 2006-095316 A | 4/2006 |
| JP | 2011125195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A3 | 9/2002 |
| WO | 2006/021269 A1 | 3/2006 |
| WO | 2005110264 A3 | 4/2006 |
| WO | 2007118608 A1 | 10/2007 |
| WO | 2008/040483 A1 | 4/2008 |
| WO | 2011/018154 A1 | 2/2011 |

OTHER PUBLICATIONS

International Search Report PCT/US2013/065659 dated Jan. 8, 2014.
International Search Report PCT/US2013/064551 dated Jan. 22, 2014.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.

(56) References Cited

OTHER PUBLICATIONS

Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C..
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 13/421,373, filed Mar. 15, 2012, John R. Twomey.
U.S. Appl. No. 13/430,325, filed Mar. 26, 2012, William H. Nau, Jr.
U.S. Appl. No. 13/433,924, filed Mar. 29, 2012, Keir Hart.
U.S. Appl. No. 13/448,577, filed Apr. 17, 2012, David M. Garrison.
U.S. Appl. No. 13/460,455, filed Apr. 30, 2012, Luke Waaler.
U.S. Appl. No. 13/461,335, filed May 1, 2012, James D. Allen, IV.
U.S. Appl. No. 13/461,378, filed May 1, 2012, James D. Allen, IV.
U.S. Appl. No. 13/461,397, filed May 1, 2012, James R. Unger.
U.S. Appl. No. 13/461,410, filed May 1, 2012, James R. Twomey.
U.S. Appl. No. 13/466,274, filed May 8, 2012, Stephen M. Kendrick.
U.S. Appl. No. 13/467,767, filed May 9, 2012, Duane E. Kerr.
U.S. Appl. No. 13/470,775, filed May 14, 2012, James D. Allen, IV.
U.S. Appl. No. 13/482,589, filed May 29, 2012, Eric R. Larson.
U.S. Appl. No. 13/483,733, filed May 30, 2012, Dennis W. Butcher.
U.S. Appl. No. 13/537,517, filed Jun. 29, 2012, David N. Heard.
U.S. Appl. No. 13/537,577, filed Jun. 29, 2012, Tony Moua.
U.S. Appl. No. 13/708,335, filed Dec. 7, 2012, Dumbauld.
U.S. Appl. No. 13/731,674, filed Dec. 31, 2012, Siebrecht.
U.S. Appl. No. 13/799,173, filed Mar. 13, 2013, Larson.
U.S. Appl. No. 13/803,636, filed Mar. 14, 2013, Kerr.
U.S. Appl. No. 13/803,762, filed Mar. 14, 2013, Kerr.
U.S. Appl. No. 13/803,884, filed Mar. 14, 2013, Kerr.
U.S. Appl. No. 13/804,010, filed Mar. 14, 2013, Kerr.
U.S. Appl. No. 13/833,823, filed Mar. 15, 2013, Garrison.
U.S. Appl. No. 13/834,703, filed Mar. 15, 2013, Garrison.
U.S. Appl. No. 13/835,004, filed Mar. 15, 2013, Twomey.
U.S. Appl. No. 13/838,945, filed Mar. 15, 2013, Stoddard.
U.S. Appl. No. 13/868,732, filed Apr. 23, 2013, Mueller.
U.S. Appl. No. 13/893,527, filed May 14, 2013, Horner.
U.S. Appl. No. 13/903,091, filed May 28, 2013, Nau.
U.S. Appl. No. 13/903,116, filed May 28, 2013, Nau.
U.S. Appl. No. 13/903,223, filed May 28, 2013, Payne.
U.S. Appl. No. 13/909,362, filed Jun. 4, 2013, Kerr.
U.S. Appl. No. 13/911,674, filed Jun. 6, 2013, Kerr.
U.S. Appl. No. 13/920,643, filed Jun. 18, 2013, Nau.
U.S. Appl. No. 13/922,377, filed Jun. 20, 2013, Allen.
U.S. Appl. No. 13/922,975, filed Jun. 20, 2013, McKenna.
U.S. Appl. No. 13/933,409, filed Jul. 2, 2013, Mueller.
U.S. Appl. No. 13/933,683, filed Jul. 2, 2013, Nau.
U.S. Appl. No. 13/936,510, filed Jul. 8, 2013, Kerr.
U.S. Appl. No. 13/947,991, filed Jul. 22, 2013, Kerr.
U.S. Appl. No. 13/969,204, filed Aug. 16, 2013, Bucciaglia.
U.S. Appl. No. 13/969,278, filed Aug. 16, 2013, Kerr.
U.S. Appl. No. 14/017,572, filed Sep. 4, 2013, Arya.
U.S. Appl. No. 14/019,031, filed Sep. 5, 2013, Garrison.
U.S. Appl. No. 14/019,094, filed Sep. 5, 2013, Garrison.

\* cited by examiner

DEPLOYMENT MECHANISMS FOR SURGICAL INSTRUMENTS

CROSS REFERENCE TO RELATED APPLICATION

The present application claims the benefit of and priority to U.S. Provisional Application Ser. No. 61/726,988, filed on Nov. 15, 2012, the entire contents of which are incorporated herein by reference.

BACKGROUND

1. Technical Field

The present disclosure relates to surgical instruments and, more particularly, to deployment mechanisms for deploying, e.g., actuating, multiple components of a surgical instrument.

2. Background of Related Art

Many surgical instruments include one or more movable handles, levers, actuators, triggers, etc. for actuating and/or manipulating one or more functional components of the surgical instrument. For example, a surgical forceps may include a movable handle that is selectively compressible relative to a stationary handle for moving first and second jaw members of the forceps between spaced-apart and approximated positions for grasping tissue therebetween. Such a forceps may further include a trigger for selectively deploying a knife between the jaw members to cut tissue grasped therebetween.

In general, each functional component provided with a surgical instrument requires a corresponding deployment structure for actuating that particular component, e.g., a movable handle for moving the jaw members or a trigger for deploying the knife. As additional functional components are added to the surgical instrument, either additional deployment structures or a deployment structure capable of actuating more than one component is required.

SUMMARY

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

In accordance with aspects of the present disclosure, a surgical instrument is provided that generally includes a first drive assembly, a second drive assembly, and a deployment mechanism. The first drive assembly is coupled to a first component and is configured to translate a first longitudinal distance X1 to deploy the first component. The second drive assembly is coupled to a second component and is configured to translate a second longitudinal distance X2 to deploy the second component. The first longitudinal distance X1 is greater than the second longitudinal distance X2, although this configuration may be reversed. The deployment mechanism is operably coupled to both the first and second drive assemblies and is configured to move from a first position to a second position to translate the first and second drive assemblies the respective first and second longitudinal distances X1 and X2 to deploy the first and second components.

In one aspect, the deployment mechanism is pivotable about a pivot from the first position to the second position.

In another aspect, the first drive assembly is coupled to the deployment mechanism at a first radial distance D1 from the pivot, and the second drive assembly is coupled to the deployment mechanism at a second radial distance D2 from the pivot. The first radial distance D1 is greater than the second radial distance D2, although this configuration may be reversed.

In yet another aspect, each of the first and second drive assemblies is coupled to the deployment mechanism via a pin and slot engagement.

In still another aspect, an actuator is provided. The actuator is coupled to the deployment mechanism and is selectively actuatable to move the deployment mechanism from the first position to the second position to deploy the first and second components.

In still yet another aspect, the deployment mechanism is configured to simultaneously translate the first and second drive assemblies the respective first and second longitudinal distances X1 and X2 to simultaneously deploy the first and second components.

Another surgical instrument provided in accordance with aspects of the present disclosure includes a deployment member, a first drive assembly, and a second drive assembly. The deployment member is coupled to a pivot and extends therefrom. The deployment member is rotatable about the pivot from a first position to a second position. The deployment member defines a first slot having a center that is disposed a first radial distance D1 from the pivot and a second slot having a center that is disposed a second radial distance D2 from the pivot. The first radial distance D1 is greater than the second radial distance D2, although this configuration may be reversed. The first drive assembly has a proximal end including a first pin slidably disposed within the first slot, and a distal end coupled to a first component. The second drive assembly has a proximal end including a second pin slidably disposed within the second slot, and a distal end coupled to a second component. Rotational movement of the deployment member from the first position to the second position urges the first drive assembly to translate a first longitudinal distance X1 to deploy the first component and the second drive assembly to translate a second longitudinal distance X2 to deploy the second component. The first longitudinal distance X1 is greater than the second longitudinal distance X2, although this configuration may be reversed.

In an aspect, the surgical instrument further includes an actuator coupled to the deployment member. The actuator is selectively actuatable to rotate the deployment member from the first position to the second position to deploy the first and second components.

In another aspect, the actuator is coupled to the pivot and is rotatable about the pivot from an un-actuated position to an actuated position to rotate the deployment member from the first position to the second position.

In still yet another aspect, rotational movement of the deployment member from the first position to the second position simultaneously urges the first drive assembly to translate the first longitudinal distance X1 to deploy the first component and the second drive assembly to translate the second longitudinal distance X2 to deploy the second component.

A surgical instrument provided in accordance with aspects of the present disclosure includes an end effector assembly configured to apply energy to tissue to treat tissue, an insulative sleeve member, an energizable rod member, and a deployment mechanism. The insulative sleeve member is movable a first longitudinal distance X1 relative to the end effector assembly from a first retracted position to a first deployed position to substantially electrically insulate the end effector assembly from a surrounding area. The energizable rod member is selectively movable a second longitudinal distance X2 relative to the end effector assembly from a second retracted position to a second deployed position. The energizable rod member is configured to apply energy to tissue to treat tissue when disposed in the second deployed position. The first longitudinal distance X1 is greater than the second longitudinal distance X2, although this configuration may be reversed. The deployment mechanism is coupled to the insulative sleeve member and the energizable rod member and is configured for selective movement from a first position to a second position to move the insulative sleeve member and the energizable rod member the respective first and second longitudinal distances X1 and X2 from their respective retracted positions to their respective deployed positions.

In one aspect, the deployment mechanism includes a deployment member coupled to a pivot and extending from the pivot. The deployment member is rotatable about the pivot from the first position to the second position to deploy the insulative sleeve member and the energizable rod member.

In another aspect, the insulative sleeve member is coupled to the deployment member a first radial distance D1 from the pivot and the energizable rod member is coupled to the deployment member a second radial distance D2 from the pivot. The first radial distance D1 is greater than the second radial distance D2, although this configuration may be reversed.

In yet another aspect, the surgical instrument further includes a sleeve-drive assembly and a rod-drive assembly. The sleeve-drive assembly interconnects the deployment mechanism and the insulative sleeve member and is configured to urge the insulative sleeve member to move the first longitudinal distance X1 upon movement of the deployment mechanism from the first position to the second position. The rod-drive assembly interconnects the deployment mechanism and the energizable rod member and is configured to urge the energizable rod member to move the second longitudinal distance X2 upon movement of the deployment mechanism from the first position to the second position.

In still another aspect, an actuator is provided. The actuator is coupled to the deployment mechanism and is selectively movable from an un-actuated position to an actuated position to move the deployment mechanism from the first position to the second position.

In yet another aspect, the actuator includes a lever rotatable about a pivot between the un-actuated position and the actuated position.

In still yet another aspect, the end effector assembly includes first and second jaw members. One or both of the jaw members is movable relative to the other from a spaced-apart position to an approximated position for grasping tissue therebetween. One or both of the jaw members is configured to connect to a source of energy for applying energy to tissue grasped therebetween.

In another aspect, the insulative sleeve member is positioned proximally of the end effector assembly in its retracted position and is substantially disposed about the end effector assembly in its deployed position.

In another aspect, the energizable rod member is disposed within the end effector assembly in its retracted position and at least partially extends from the end effector assembly in its deployed position.

In still yet another aspect, the deployment mechanism is configured to simultaneously move the insulative sleeve member and the energizable rod member the respective first and second longitudinal distances X1 and X2 from their respective retracted positions to their respective deployed positions.

BRIEF DESCRIPTION OF THE DRAWINGS

Various aspects of the present disclosure are described herein with reference to the drawings wherein like reference numerals identify similar or identical elements.

DETAILED DESCRIPTION

Referring now to FIGS. 1-7, a forceps provided in accordance with the present disclosure is shown generally identified by reference numeral 10. Forceps 10 is configured to operate in both a bipolar mode, e.g., for grasping, treating, and/or dissecting tissue, and a monopolar mode, e.g., for treating and/or dissecting tissue. As such, and as will be described in greater detail below, forceps 10 includes multiple assemblies and components configured to facilitate the various operations of forceps 10. More specifically, in order to facilitate simultaneous actuation, movement, and/or deployment of one or more assemblies and/or components of forceps 10, a differential deployment mechanism 300 is provided that allows for the actuation, movement, and/or deployment of multiple assemblies and/or components using a single actuation member, e.g., a trigger, lever, handle, etc.

Although differential deployment mechanism 300 is shown and configured for use with monopolar assembly 200 of forceps 10, it is contemplated that differential deployment mechanism 300 be configured for use with any suitable surgical instrument or portion thereof for actuating, moving, and/or deploying multiple assemblies and/or components using a single actuation member. Obviously, different connections and considerations apply to each particular instrument and the assemblies and/or components thereof; however, the aspects, features, and operating characteristics of differential deployment mechanism 300 remain generally consistent regardless of the particular instrument, assemblies, and/or components provided. For the purposes herein, forceps 10 will be generally described.

Continuing with reference to FIGS. 1-7, forceps 10 includes a shaft 12 defining a longitudinal axis "X-X," a housing 20, a handle assembly 30, a trigger assembly 60, a rotating assembly 70, a lever assembly 80, an end effector assembly 100, and a monopolar assembly 200. Shaft 12 defines a distal end 14 that is configured to mechanically engage end effector assembly 100 and a proximal end 16 that mechanically engages housing 20. Housing 20 is configured to house the internal working components of forceps 10, which will be described in detail below.

Referring to FIGS. 2A-3B, end effector assembly 100 is shown attached at a distal end 14 of shaft 12 and includes a pair of opposing jaw members 110 and 120 pivotably coupled to one another about a pivot 102. Each of the jaw members 110 and 120 includes an electrically-insulative outer jaw housing 111, 121 and an electrically-conductive plate 112, 122 disposed atop respective jaw housings 111, 121, although other configurations are also contemplated. Plates 112, 122 of jaw members 110, 120, respectively, are adapted to connect to any suitable source of energy (not explicitly shown), e.g., electrosurgical, ultrasonic, microwave, light, etc., via wires 2a (FIG. 4), for conducting energy therebetween and through tissue grasped between jaw members 110, 120 to treat, e.g., seal, tissue. In one particular configuration, end effector assembly 100 defines a bipolar configuration wherein plate 112 is charged to a first electrical potential and plate 122 is charged to a second, different electrical potential such that an electrical potential gradient is created for conducting energy between plates 112, 122 and through tissue grasped therebetween for treating e.g., sealing, tissue. Activation switch 90 (FIG. 1) is coupled to wires 2a (FIG. 4), thus allowing the user to selectively apply energy to plates 112, 122 of end effector assembly 100 during a bipolar mode of operation.

End effector assembly 100 is designed as a unilateral assembly, i.e., where jaw member 120 is fixed relative to shaft 12 and jaw member 110 is movable relative to shaft 12 and fixed jaw member 120. However, end effector assembly 100 may alternatively be configured as a bilateral assembly, i.e., where both jaw member 110 and jaw member 120 are movable relative to one another and to shaft 12. In some embodiments, a knife channel 115, 125 (FIGS. 8A-8D) may be defined within one or both of jaw members 110, 120 to permit reciprocation of knife 184 therethrough, e.g., upon actuation of trigger 62 of trigger assembly 60.

Figures 1, 2A:
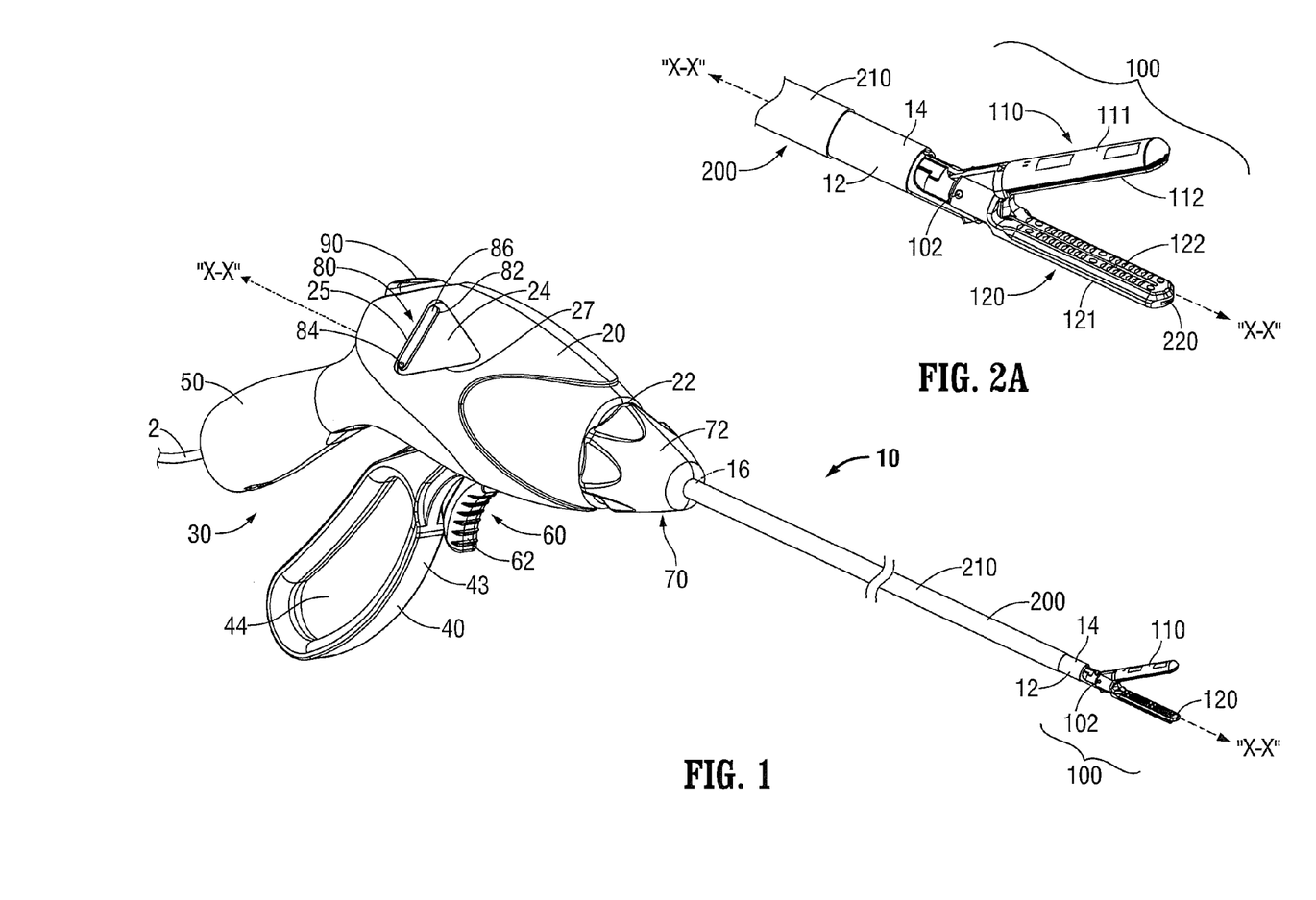
FIG. 1 is a front, perspective view of an endoscopic surgical forceps configured for use in accordance with the present disclosure.
FIG. 2A is an enlarged, perspective view of an end effector assembly of the forceps of FIG. 1.
Figure 2B:
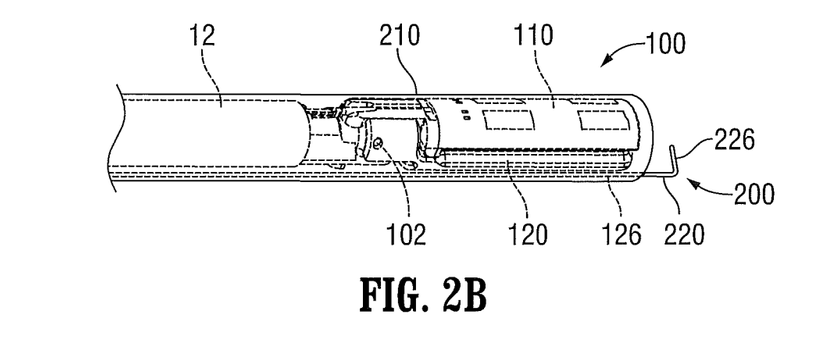
FIG. 2B is an enlarged, perspective view of the end effector assembly of FIG. 2A, wherein the jaw members are disposed in an approximated position and wherein the monopolar assembly is disposed in a deployed position.
Figure 3A:
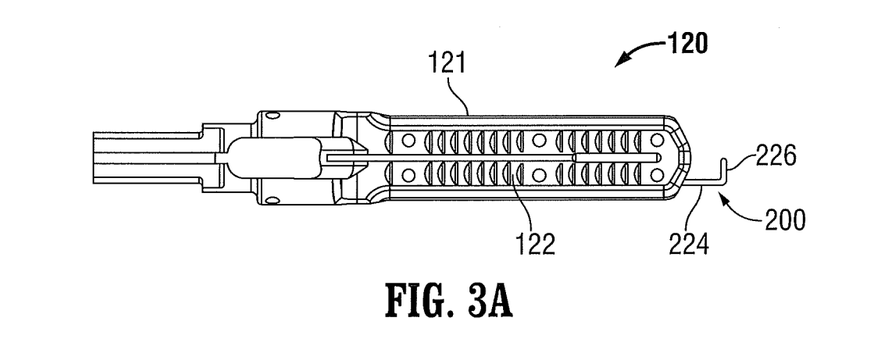
FIG. 3A is a top view of one of the jaw members of the end effector assembly of FIG. 2A.
Figure 3B:
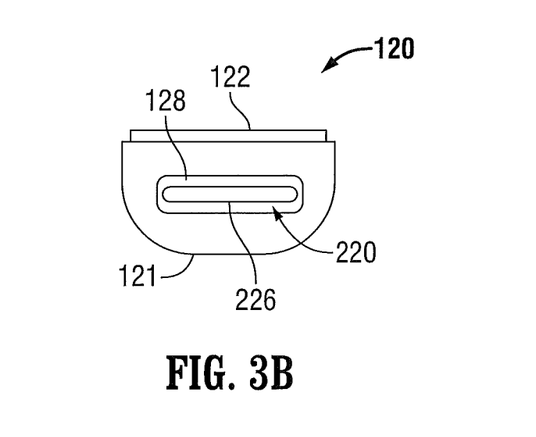
FIG. 3B is a front view of the jaw member of FIG. 3A.

With continued reference to FIGS. 2A-3B, and to FIGS. 3A-3B in particular, one of the jaw members 110, 120 of end effector assembly 100, e.g., jaw member 120, is configured to house energizable rod member 220 of monopolar assembly 200 therein. More specifically, jaw member 120 defines an elongated lumen 126 (FIGS. 8A-8D) extending longitudinally through insulative jaw housing 121 that is configured to slidably receive body 224 of energizable rod member 220 of monopolar assembly 200. A transversely-extending recess 128 may also be defined within jaw housing 121 of jaw member 120 at the distal end thereof. Recess 128 is disposed in communication with lumen 126 (FIGS. 8A-8D) and is configured to receive the distal tip 226 of energizable rod member 220 of monopolar assembly 200 when monopolar assembly 200 is disposed in the retracted position. Distal tip 226 may be hook-shaped (as shown), or may define any other suitable configuration, e.g., linear, circular, angled, etc. In the retracted position of monopolar assembly 200, energizable rod member 220 is disposed within jaw housing 121 such that energizable rod member 220 is electrically insulated from electrically-conductive plates 112, 122 of jaw members 110, 120, respectively. Alternatively, energizable rod member 220 may only be insulated from plate 112. In such configurations, energizable rod member 220 is capable of being energized to the same polarity as plate 122. Upon deployment of monopolar assembly 200 to the deployed position, distal tip 226 of energizable rod member 220 extends distally from recess 128, and body 224 of energizable rod member 220 extends at least partially distally from lumen 126 (FIG. 8D), as shown in FIG. 3A. Monopolar assembly 200 will be described in greater detail below.

Figure 4:
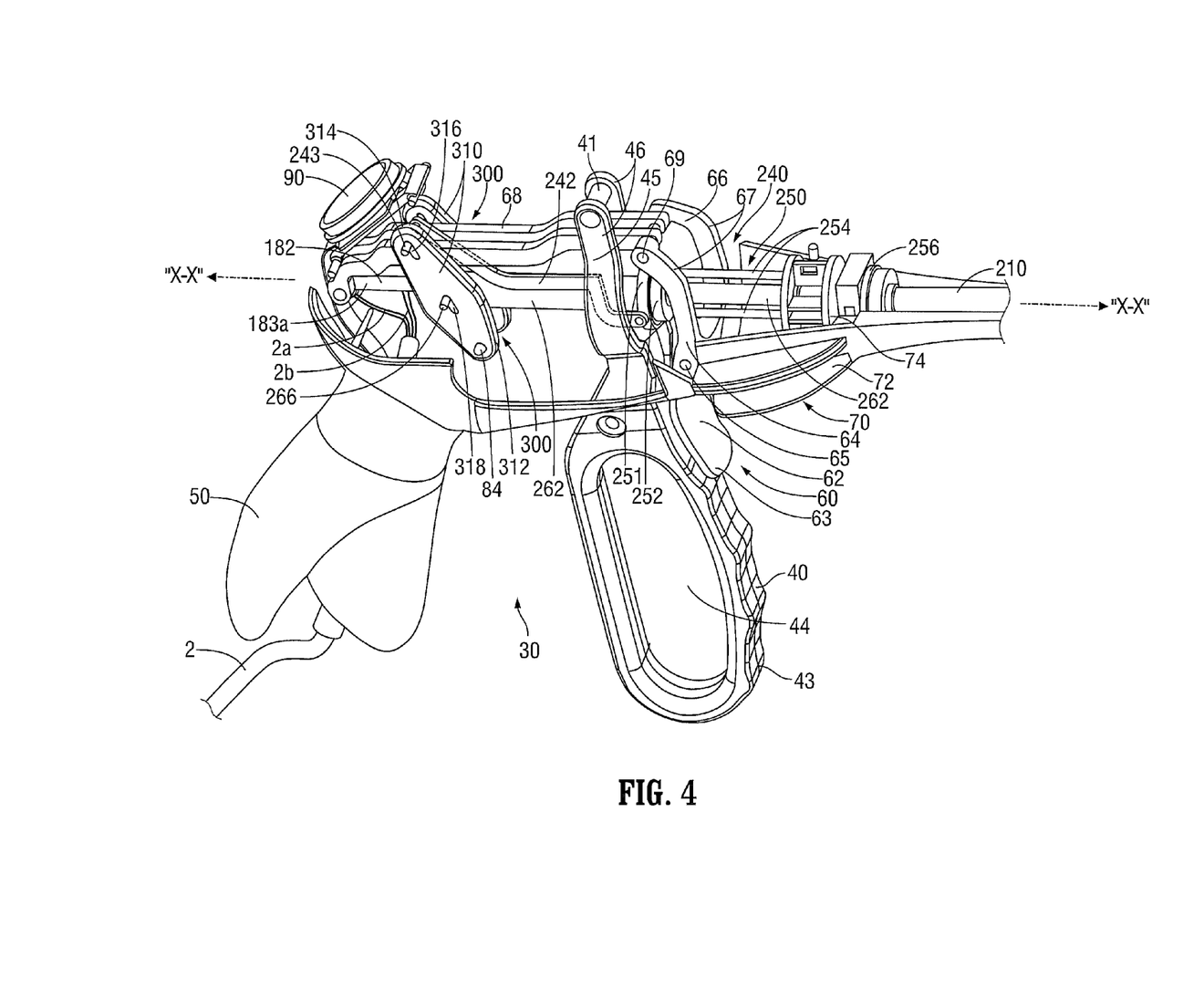
FIG. 4 is a side, perspective, cut-away view of the housing of the forceps of FIG. 1 showing the internal components disposed within the housing.
Figure 5:
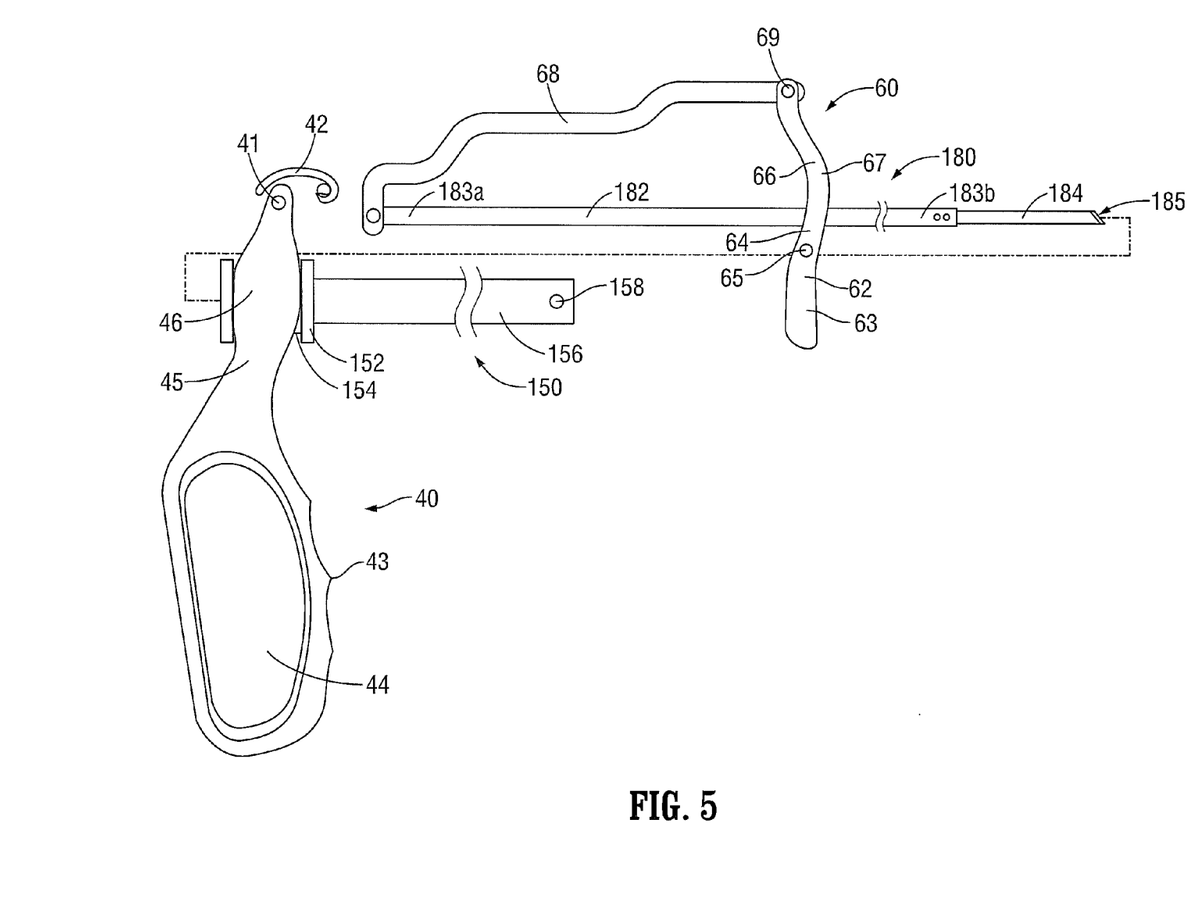
FIG. 5 is an exploded, side view of a drive assembly and knife assembly of the forceps of FIG. 1.

With reference to FIGS. 1, 4, and 5, handle assembly 30 includes a movable handle 40 and a fixed handle 50. Fixed handle 50 is integrally associated with housing 20 and movable handle 40 is movable relative to fixed handle 50. Movable handle 40 is pivotably coupled to housing 20 via pivot 41 and is pivotable about pivot 41 and relative to fixed handle 50 between an initial position, wherein movable handle 40 is spaced from fixed handle 50, and a compressed position, wherein movable handle 40 is compressed towards fixed handle 50. A biasing member 42 (see FIG. 5) may be provided to bias movable handle 40 towards the initial position. Movable handle 40 is ultimately connected to a drive assembly 150 that, together, mechanically cooperate to impart movement of jaw members 110, 120 between a spaced-apart position (FIG. 8A) and an approximated position (FIG. 8B) to grasp tissue between electrically-conductive plates 112, 122 of jaw members 110, 120, respectively. Drive assembly 150 will be described in greater detail below.

Turning now to FIGS. 1, 4, and 5, as mentioned above, drive assembly 150 interconnects movable handle 40 and end effector assembly 100. Movable handle 40 includes a handle portion 43 defining a finger hole 44 and a bifurcated arm 45 extending upwardly from handle portion 43 and into housing 20. Arm 45 is bifurcated to define first and second spaced-apart flanges 46 (see FIG. 4), that are pivotably coupled to housing 20 at the free ends thereof via pivot 41. Flanges 46 extend on either side of drive assembly 150 and are coupled thereto to facilitate movement of jaw members 110, 120 between the spaced-apart position and approximated positions. More specifically, flanges 46 extend upwardly on either side of mandrel 152 (removed from FIG. 4 but shown in FIG. 5) and are disposed within lateral slots 154 defined within mandrel 152 such that pivoting of movable handle 40 about pivot 41 between the initial and compressed positions effects corresponding longitudinal translation of mandrel 152.

Mandrel 152 is fixedly engaged about the proximal end of an elongated drive member 156. Elongated drive member 156 extends distally from housing 20 and through shaft 12, ultimately coupling to end effector assembly 100. More specifically, elongated drive member 156 includes a transverse drive pin 158 disposed towards a distal end thereof that is pivotably coupled to the movable jaw member(s) 110, 120, e.g., jaw member 110, such that proximal translation of elongated drive member 156 pulls jaw member 110 to pivot relative to jaw member 120 towards the approximated position, while distal translation of elongated drive member 156 pushers jaw member 110 to pivot relative to jaw member 120 towards the spaced-apart position. As such, pivoting of movable handle 40 between the initial and compressed positions effects movement of jaw members 110, 120 between the spaced-apart and approximated positions.

Trigger assembly 60, as shown in FIGS. 1, 4, and 5, is coupled to knife assembly 180 such that trigger 62 is selectively actuatable from an un-actuated, distal position to an actuated, proximal position to advance knife 184 from a retracted position (FIG. 8B), wherein knife 184 is disposed proximally of jaw members 110, 120, to an extended position, wherein knife 184 extends between jaw members 110, 120 and through knife channels 115, 125, respectively (FIG. 8C), to cut tissue grasped between jaw members 110, 120. Trigger assembly 60 will be described in greater detail below. Knife assembly 180 includes a knife drive rod 182 defining proximal and distal ends 183a, 183b, respectively. Proximal end 183a of knife drive rod 182 is coupled to connector 68 of trigger assembly 60. Knife drive rod 182 extends distally through rod drive bar 262 of rod-drive assembly 260 (FIGS. 6-7), which is disposed within elongated drive member 156 of drive assembly 150 and shaft 12, ultimately engaging the proximal end of knife 184. Knife 184 defines a distal cutting edge 185 configured to facilitate the cutting of tissue upon translation of knife 184 therethrough.

Trigger assembly 60 includes a trigger 62 having a toggle member 63 and a bifurcated arm 66 extending upwardly from toggle member 63 and into housing 20. Trigger 62 is pivotably coupled to housing 20 via pivot 65, which extends through an intermediate portion 64 of trigger 62. Arm 66 is bifurcated to define first and second spaced-apart flanges 67 to permit passage of arm 66 about drive assembly 150. A pin 69 pivotably couples flanges 67 of trigger 62 to connector 68. Connector 68 extends proximally through housing 20, ultimately coupling to the proximal end of knife drive rod 182 of knife assembly 180. Accordingly, upon pivoting of trigger 62 about pivot pin 65 and relative to housing 20 from the un-actuated position towards the actuated position, flanges 67 are rotated to pull connector 68 distally such that knife drive rod 182 is pushed distally to translate knife 184 from the retracted position towards the extended position. On the other hand, upon return of trigger 62 towards the un-actuated position, flanges 67 are rotated to push connector 68 proximally such that knife drive rod 182 is pulled proximally to translate knife 184 back towards the retracted position. A biasing member (not shown) may be provided for biasing trigger 62 towards the un-actuated position, thereby biasing knife 184 towards the retracted position.

With reference to FIGS. 1 and 4, rotating assembly 70 includes a rotating member 72 that is rotatably coupled to a distal nose portion 22 of housing 20 and is rotatable in either direction about longitudinal axis "X-X" and relative to housing 20 to rotate end effector assembly 100 and monopolar assembly 200 about longitudinal axis "X-X" and relative to housing 20. Rotating assembly 70 further includes an engagement member 74 disposed within rotating member 72 and fixedly engaged about shaft 12 such that rotation of rotating member 72 effects similar rotation of shaft 12 and, thus, end effector assembly 100. Engagement member 74 further includes a pair of lumens (not shown) configured to receive the substantially parallel bars 254 of transition component 250 of sleeve-drive assembly 240 (FIGS. 6-7) of monopolar assembly 200 such that rotation of rotating member 72 effects similar rotation of transition component 250 (FIGS. 6-7), insulative sleeve 210, and energizable rod member 220 (FIG. 3A) of monopolar assembly 200. However, the rotatable coupling of first and second proximal collars 251, 252 of transition component 250 (see FIGS. 6-7) allows the remaining components of sleeve-drive assembly 240 (FIGS. 6-7) to remain stationary despite rotation of rotating assembly 70, so as not to interfere with the operation of differential deployment mechanism 300 (FIGS. 6-7) and/or lever assembly 80, as will be described below.

Referring to FIG. 1, lever assembly 80 is shown. Although lever assembly 80 is shown disposed on only one side of housing 20, lever assembly 80 may be configured to define a symmetrical configuration having substantially similar components disposed on either side of housing 20, thus allowing actuation of lever assembly 80 from either side of housing 20. However, for purposes of simplicity, only one side of lever assembly 80 will be described herein.

Figure 6:
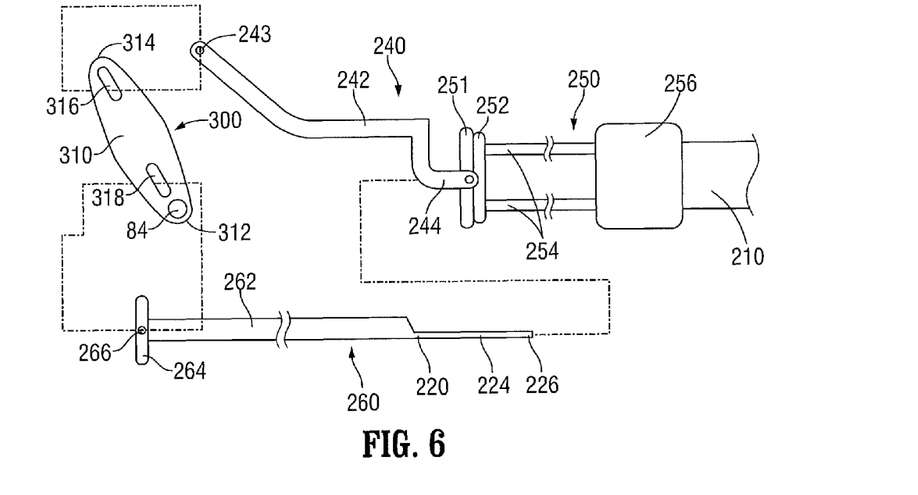
FIG. 6 is an exploded, side view of the monopolar assembly of the forceps of FIG. 1.
Figure 7:
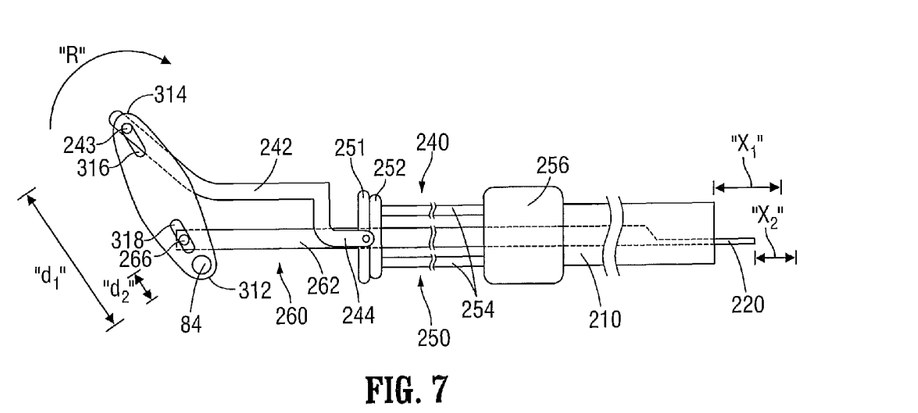
FIG. 7 is a side view of the monopolar assembly of FIG. 6.

Lever assembly 80 is disposed within a recess 24 defined on an exterior side surface of housing 20 (although lever assembly 80 may also be positioned at any other suitable location) and includes a lever 82 that is rotatable about a pivot 84 between a first position, wherein free end 86 of lever 82 is disposed at a proximal end 25 of recess 24, and a second position, wherein free end 86 of lever 82 is disposed at a distal end 27 of recess 24. In configurations where lever assembly 80 defines a symmetrical configuration, a pair of levers 82 are provided on either side of housing 20, each of which is coupled to one end of pivot 84. Pivot 84 is rotatably coupled to housing 20 and extends through housing 20, ultimately coupling to differential deployment mechanism 300 (FIGS. 6-7). Differential deployment mechanism 300 (FIGS. 6-7), in turn, as will be described in greater detail below, is coupled to monopolar assembly 200 such that, upon pivoting of lever 82 from the first position to the second position, insulative sleeve 210 and energizable rod member 220 (FIG. 3A) of monopolar assembly 200 are moved between their respective retracted and deployed positions (see FIGS. 2A-2B).

With reference to FIGS. 1-4 and 6-7, monopolar assembly 200 includes an insulative sleeve 210 and an energizable rod member 220. Insulative sleeve 210 is slidably disposed about shaft 12 and is configured for translation about and relative to shaft 12 between a retracted position (FIGS. 2A and 8A-8C), where insulative sleeve 210 is disposed proximally of end effector assembly 100, and a deployed position (FIGS. 2B and 8D), wherein insulative sleeve 210 is substantially disposed about end effector 100 so as to electrically insulate plates 112, 122 of jaw members 110, 120, respectively, from the surroundings of insulative sleeve 210. Energizable rod member 220, as mentioned above, is movable from a retracted position, wherein energizable rod member 220 is substantially disposed within jaw housing 121, and deployed position, wherein energizable rod member 220 extends distally from jaw housing 121 (see FIGS. 2B and 3A). Wires 2b, which extend from electrosurgical cable 2, through housing 20, are coupled to energizable rod member 220 to provide energy to energizable rod member 220, e.g., upon actuation of activation switch 90 (FIG. 1) in a monopolar mode of operation, for treating tissue using monopolar energy.

With particular reference to FIGS. 4 and 6-7, monopolar assembly 200 further includes a sleeve-drive assembly 240 and a rod-drive assembly 260. Sleeve-drive assembly 240 is disposed within housing 20 and includes an elongated linkage 242 and a transition component 250. Elongated linkage 242 includes a proximal end having a transverse pin 243 extending therefrom that couples linkage 242 to differential deployment mechanism 300, as will be described in greater detail below, and a bifurcated distal end 244 that is pivotably coupled to transition component 250. Transition component 250 includes first and second proximal collars 251, 252. First proximal collar 251 is pivotably coupled to bifurcated distal end 244 of linkage 242 at opposed annular positions on first proximal collar 251. Second proximal collar 252 is rotatably engaged to first proximal collar 251, thus allowing rotation of transition component 250 relative to linkage 242 upon rotation of rotating member 72 (FIGS. 1 and 4), as mentioned above. Second proximal collar 252 includes a pair of substantially parallel bars 254 that extend distally therefrom, through rotating assembly 70, ultimately coupling to ferrule 256. Ferrule 256 is fixedly disposed, e.g., mechanically engaged, about the proximal end of insulative sleeve 210. Accordingly, upon distal advancement of linkage 242, transition component 250 is translated distally to similarly translate insulative sleeve 210 distally relative to end effector assembly 100, e.g., from the retracted position (FIGS. 2A and 8C) to the deployed position (FIGS. 2B and 8D).

Rod-drive assembly 260 includes a rod drive bar 262 that extends distally through housing 20 and elongated drive member 156 of drive assembly 150, which extends through shaft 12. Rod drive bar 262 is ultimately coupled, e.g., integrally formed, mechanically engaged, etc., to the proximal end of energizable rod member 220 such that translation of rod drive bar 262 effects similar translation of energizable rod member 220. More specifically, rod-drive assembly 260 is configured such that, upon actuation of differential deployment mechanism 300, as will be described below, rod drive member 262 is translated distally to translate energizable rod member 220 from the retracted position (FIGS. 2A and 8C) to the deployed position (FIGS. 2B and 8D). Rod drive bar 262 includes a proximal ring 264 rotatably disposed at the proximal end thereof. A transverse pin 266 extends outwardly from either side of proximal ring 264 for coupling rod-drive assembly 260 to differential deployment mechanism 300. The rotatable coupling of proximal ring 264 to rod drive bar 262 allows rod drive bar 262 to rotate upon rotation of rotating member 72 of rotating assembly 70, without rotating proximal ring 264, thereby maintaining the operative engagement between proximal ring 264 and differential deployment mechanism 300.

Referring to FIGS. 1, 4, 6, and 7, differential deployment mechanism 300 interconnects lever assembly 80 and monopolar assembly 200. More particularly, differential deployment mechanism 300 couples lever assembly 80 to both sleeve-drive assembly 240 and rod-drive assembly 260 of monopolar assembly 200 such that, upon pivoting of lever 82 from the first position to the second position, both insulative sleeve 210 and energizable rod member 220 of monopolar assembly 200 are translated from their respective retracted positions to their respective deployed positions, despite the different deployment lengths of insulative sleeve 210 and energizable rod member 220. That is, differential deployment mechanism 300 enables actuation of lever 82 to effect both translation of insulative sleeve 210 the distance "$X_1$" (FIG. 8D) from the retracted position, wherein insulative sleeve 210 is positioned proximally of end effector assembly 100, to the deployed position, wherein insulative sleeve 210 is disposed about jaw members 110, 120, and the translation of rod member 220 the distance "$X_2$" (FIG. 8D) from the retracted position, wherein rod member 220 is disposed within jaw member 120, to the deployed position, wherein rod member 220 extends distally from jaw member 120. However, as mentioned above, differential deployment mechanism 300 may alternatively or additionally be configured for use with any of the other components of forceps 10, e.g., drive assembly 150 and/or trigger assembly 60, or any suitable components of any surgical instrument, to facilitate the deployment of multiple components through a single actuator, even where the components require different amounts, distances, and/or degrees of deployment.

Continuing with reference to FIGS. 4, 6, and 7, differential deployment mechanism 300 includes a pair of arms 310 disposed within housing 20 on opposed sides thereof. Each arm 310 is engaged about pivot 84 of lever assembly 80 at the first end 312 thereof such that rotation of pivot 84 relative to housing 20, e.g., via rotation of lever 82, effects rotation of second ends 314 of arms 310 about first ends 312 thereof. Each arm 310 further includes first and second slots 316, 318, respectively, defined therethrough. First slots 316 are defined towards the free, second ends 314 of arms 310 and are disposed a first distance "$D_1$" (as measured from a center of the slot) from pivot 84. First slots 316 are configured to receive transverse pin 243 of sleeve-drive assembly 240 therein. Second slots 318 are defined through the intermediate portions of arms 310, e.g., between the first and second ends 312, 314, respectively, thereof, and are disposed a second distance "$D_2$" (as measured from a center of the slot) from pivot 84. Second slots 318 are configured to receive transverse pin 266 of rod-drive assembly 260 therein.

As mentioned above, first slots 316, the centers of which are disposed a distance "$D_1$" from pivot 84, are configured to receive transverse pin 243 of sleeve-drive assembly 240, while second slots 318, the centers of which are disposed a distance "$D_2$" from pivot 84, are configured to receive transverse pin 266 of rod-drive assembly 260 therein. As a result of this configuration, the radius of curvature of arms 310 in the vicinity of first slots 316 (where transverse pin 243 of sleeve-drive assembly 240 is disposed) is greater than the radius of curvature of arms 310 in the vicinity of second slots 318 (where transverse pin 266 of rod-drive assembly 260 is disposed). Thus, the arc length, e.g., travel distance, of transverse pin 243 of sleeve-drive assembly 240 is greater than that of transverse pin 266 of rod-drive assembly 260 for any given angular displacement, e.g., for any given degree of rotation of arms 310 about pivot 84. As such, sleeve-drive assembly 240 is translated a greater distance relative to rod-drive assembly 260 upon rotation of arms 310 about pivot 84. The particular deployment distances "$X_1$" and "$X_2$" of sleeve-drive assembly 240 and rod-drive assembly 260, respectively, are set via setting the distances "$D_1$" and "$D_2$" and the angular displacement of arms 310. Accordingly, a desired configuration suitable for a particular purpose can be achieved.

The engagement of pins 243, 266 within slots 316, 318, allows pins 243, 266 to translate along slots 316, 318, respectively, during rotation of arms 310 about pivot 84 such that the arc-travel of arms 310 (having both a longitudinal and vertical component) is converted into longitudinal translation of pins 243, 266. Longitudinal translation of pins 243, 266 the respective distances "$X_1$" and "$X_2$," in turn, effects translation of insulative sleeve 210 of monopolar assembly 200 a distance "$X_1$" (FIG. 8D) and energizable rod member 220 of monopolar assembly 200 a distance "$X_2$" (FIG. 8D), respectively. However, the drive assemblies coupled to differential deployment mechanism 300 need not be configured to linearly convert longitudinal translation thereof into corresponding longitudinal translation of the components coupled thereto. Rather, differential deployment mechanism 300 may be employed to translate two or more drive assemblies different distances so as to effect deployment or actuation of the components coupled thereto in any suitable manner. For example, differential deployment mechanism 300 may be coupled to drive assembly 150 (FIG. 5) for translating elongated drive member 156 (FIG. 5) to move jaw members 110, 120 (FIGS. 2A-2B) between the spaced-apart and approximated positions.

Figure 8A:
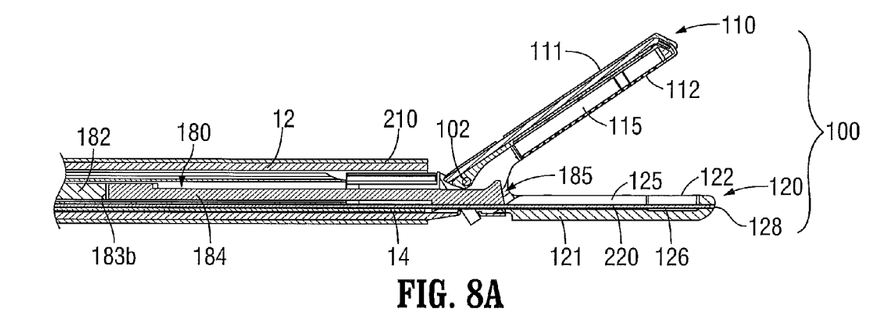
FIG. 8A is a longitudinal, cross-sectional view of the end effector assembly of FIG. 2A with the jaw members disposed in a spaced-apart position.
Figure 8B:
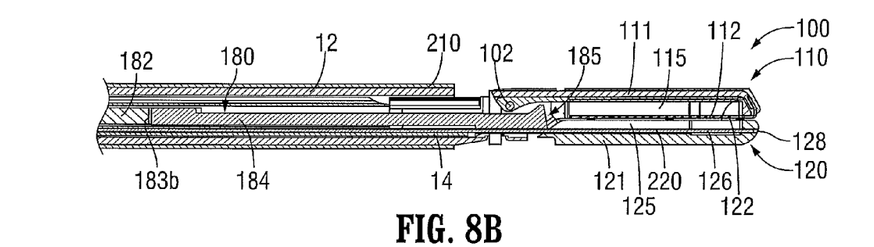
FIG. 8B is a longitudinal, cross-sectional view of the end effector assembly of FIG. 2A with the jaw members disposed in an approximated position.
Figure 8C:
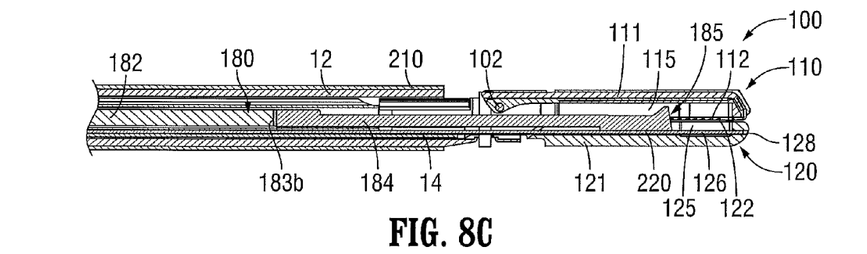
FIG. 8C is a longitudinal, cross-sectional view of the end effector assembly of FIG. 2A with the jaw members disposed in the approximated position and a knife disposed in an extended position.
Figure 8D:
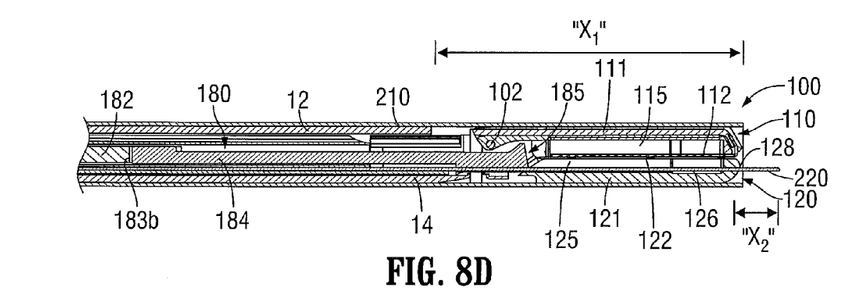
FIG. 8D is a longitudinal, cross-sectional view of the end effector assembly of FIG. 2A with a monopolar assembly disposed in a deployed position.

Turning now to FIGS. 8A-8D, in conjunction with FIGS. 1-7, the use and operation of forceps 10 in both the bipolar mode, e.g., for grasping, treating and/or cutting tissue, and the monopolar mode, e.g., for electrical/electromechanical tissue treatment, is described. Initially, with respect to the bipolar mode, as shown in FIG. 8A, jaw members 110, 120 are disposed in the spaced-apart position. In the bipolar mode, monopolar assembly 200 remains disposed in the retracted position, as shown in FIGS. 8A-8C, wherein insulative sleeve 210 is positioned proximally of jaw members 110, 120 and energizable rod member 220 is disposed in the retracted position within lumen 126 and recess 128 of jaw housing 121 of jaw member 120. With jaw members 110, 120 disposed in the spaced-apart position, end effector assembly 100 may be maneuvered into position such that tissue to be grasped, treated, e.g., sealed, and/or cut, is disposed between jaw members 110, 120. Next, movable handle 40 is depressed, or pulled proximally relative to fixed handle 50 such that jaw member 110 is pivoted relative to jaw member 120 from the spaced-apart position to the approximated position to grasp tissue therebetween, as shown in FIG. 8B. In this approximated position, energy may be supplied, e.g., via activation of switch 90, to plate 112 of jaw member 110 and/or plate 122 of jaw member 120 and conducted through tissue to treat tissue, e.g., to effect a tissue seal or otherwise treat tissue.

Once tissue treatment is complete (or to cut untreated tissue), knife 184 of knife assembly 180 may be deployed from within shaft 12 to between jaw members 110, 120, e.g., via actuation of trigger 62 of trigger assembly 60, to cut tissue grasped therebetween. More specifically, upon actuation of trigger 62, knife 184 is advanced distally from shaft 12 to extend at least partially through knife channels 115, 125 of jaw members 110, 120, respectively, to cut tissue grasped between jaw members 110, 120 (FIG. 8C). Thereafter, knife 184 may be returned to within shaft 12 and jaw members 110, 120 may be moved back to the spaced-apart position (FIG. 8A) to release the treated and/or divided tissue.

For operation of forceps 10 in the monopolar mode, movable handle 40 is first depressed relative to fixed handle 50 to pivot jaw member 110 relative to jaw member 120 from the spaced-apart position to the approximated position. With jaw members 110, 120 disposed in the approximated position, monopolar assembly 200 may be translated from the retracted position (FIGS. 2A and 8C) to the deployed position (FIGS. 2B and 8D) via actuation of lever assembly 80. More specifically, in order to translate insulative sleeve 210 and energizable rod member 220 of monopolar assembly 200 from the retracted position (FIGS. 2A and 8C) to the deployed position (FIGS. 2B and 8D), lever 82 is rotated through recess 24 of housing 20 from the proximal end 25 thereof (the first position) to the distal end 27 thereof (the second position). Rotation of lever 82 from the first position to the second position rotates arms 310 of differential deployment mechanism 300 in the direction of arrow "R" (FIG. 7). Rotation of arms 310, in turn, simultaneously: urges transverse pin 243 of sleeve-drive assembly 240 to translate distally a distance "$X_1$" such that insulative sleeve 210 is translated distally distance a distance "$X_1$" to the deployed position, wherein insulative sleeve 210 surrounds jaw members 110, 120 (FIG. 8D); and urges transverse pin 266 of rod-drive assembly 260 to translate distally a distance "$X_2$" such that energizable rod member 220 is translated distally a distance "$X_2$" to the deployed position, wherein energizable rod member 220 extends distally from jaw member 120. Although the longitudinal translation distances "$X_1$" and "$X_2$" of the respective assemblies 240, 260 effect substantially equivalent translation distances "$X_1$" and "$X_2$," of insulative sleeve 210 and energizable rod member 220, the assemblies 240, 260 may alternatively be configured to amplify or reduce the respective corresponding translation distances of insulative sleeve 210 and energizable rod member 220, depending on a particular purpose. Further, the assemblies coupled to differential deployment mechanism 300 need not be configured to effect longitudinal translation of corresponding components. For example, drive assembly 150 may be coupled to differential deployment mechanism 300 such that elongated drive member 156 is translated a particular distance to move jaw members 110, 120 between specific relative spaced-apart and approximated positions.

Once monopolar assembly 200 is disposed in the deployed position, activation switch 90 may be actuated to supply energy to energizable rod member 220 to treat, e.g., dissect, tissue. During application of energy to tissue via energizable rod member 220, forceps 10 may be moved relative to tissue, e.g., longitudinally along longitudinal axis "X-X" and/or radially therefrom, to facilitate electromechanical treatment of tissue. Alternatively, energizable rod member 220 may be used for blunt dissection, e.g., prior to energization of rod member 220. At the completion of tissue treatment, e.g., dissection, monopolar assembly 200 may be returned to the retracted position (FIG. 8C) via rotating lever 82 from the distal end 27 of recess 24 (the second position) back to the proximal end 25 thereof (the first position). Rotation of lever 82 from the second position back to the first position rotates arms 310 of differential deployment mechanism 300 in the opposite direction of arrow "R" (FIG. 7) such that insulative sleeve 210 and energizable rod member 220 are simultaneously translated proximally the respective distances "$X_1$" and "$X_2$" back to their respective retracted positions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
 a first drive assembly coupled to a first component, the first drive assembly configured to translate a first longitudinal distance X1 to deploy the first component;
 a second drive assembly coupled to a second component, the second drive assembly configured to translate a second longitudinal distance X2 to deploy the second component, wherein the first longitudinal distance X1 is greater than the second longitudinal distance X2; and
 a deployment mechanism operably coupled to both the first and second drive assemblies, the deployment mechanism configured to move from a first position to a second position to simultaneously translate the first and second drive assemblies the respective first and second longitudinal distances X1 and X2 to simultaneously deploy the first and second components.

2. The surgical instrument according to claim 1, wherein the deployment mechanism is pivotable about a pivot from the first position to the second position.

3. The surgical instrument according to claim 2, wherein the first drive assembly is coupled to the deployment mechanism at a first radial distance D1 from the pivot, wherein the second drive assembly is coupled to the deployment mechanism at a second radial distance D2 from the pivot, and wherein the first radial distance D1 is greater than the second radial distance D2.

4. The surgical instrument according to claim 3, wherein each of the first and second drive assemblies is coupled to the deployment mechanism via a pin and slot engagement.

5. The surgical instrument according to claim 1, further comprising an actuator coupled to the deployment mechanism, the actuator selectively actuatable to move the deployment mechanism from the first position to the second position to deploy the first and second components.

6. A surgical instrument, comprising:
- a deployment member coupled to a pivot and extending from the pivot, the deployment member rotatable about the pivot from a first position to a second position, the deployment member defining a first slot having a center that is disposed a first radial distance D1 from the pivot and a second slot having a center that is disposed a second radial distance D2 from the pivot, wherein the first radial distance D1 is greater than the second radial distance D2;
- a first drive assembly having a proximal end including a first pin slidably disposed within the first slot, the first drive assembly having a distal end coupled to a first component; and
- a second drive assembly having a proximal end including a second pin slidably disposed within the second slot, the second drive assembly having a distal end coupled to a second component,
- wherein rotational movement of the deployment member from the first position to the second position urges the first drive assembly to translate a first longitudinal distance X1 to deploy the first component and the second drive assembly to translate a second longitudinal distance X2 to deploy the second component, and wherein the first longitudinal distance X1 is greater than the second longitudinal distance X2.

7. The surgical instrument according to claim 6, further comprising an actuator coupled to the deployment member, the actuator selectively actuatable to rotate the deployment member from the first position to the second position to deploy the first and second components.

8. The surgical instrument according to claim 7, wherein the actuator is coupled to the pivot and is rotatable about the pivot from an un-actuated position to an actuated position to rotate the deployment member from the first position to the second position.

9. The surgical instrument according to claim 6, wherein rotational movement of the deployment member from the first position to the second position simultaneously urges the first drive assembly to translate the first longitudinal distance X1 to deploy the first component and the second drive assembly to translate the second longitudinal distance X2 to deploy the second component.

10. A surgical instrument, comprising:
- an end effector assembly configured to apply energy to tissue to treat tissue;
- an insulative sleeve member movable a first longitudinal distance X1 relative to the end effector assembly from a first retracted position to a first deployed position to substantially electrically insulate the end effector assembly from a surrounding area;
- an energizable rod member selectively movable a second longitudinal distance X2 relative to the end effector assembly from a second retracted position to a second deployed position, the energizable rod member configured to apply energy to tissue to treat tissue when disposed in the second deployed position, wherein the first longitudinal distance X1 is greater than the second longitudinal distance X2; and
- a deployment mechanism coupled to the insulative sleeve member and the energizable rod member, the deployment mechanism configured for selective movement from a first position to a second position to move the insulative sleeve member and the energizable rod member the respective first and second longitudinal distances X1 and X2 from their respective retracted positions to their respective deployed positions.

11. The surgical instrument according to claim 10, wherein the deployment mechanism includes a deployment member coupled to a pivot and extending from the pivot, the deployment member rotatable about the pivot from the first position to the second position to deploy the insulative sleeve member and the energizable rod member.

12. The surgical instrument according to claim 11, wherein the insulative sleeve member is coupled to the deployment member a first radial distance D1 from the pivot, wherein the energizable rod member is coupled to the deployment member a second radial distance D2 from the pivot, and wherein the first radial distance D1 is greater than the second radial distance D2.

13. The surgical instrument according to claim 10, further comprising:
- a sleeve-drive assembly interconnecting the deployment mechanism and the insulative sleeve member, the sleeve-drive assembly configured to urge the insulative sleeve member to move the first longitudinal distance X1 upon movement of the deployment mechanism from the first position to the second position;
- a rod-drive assembly interconnecting the deployment mechanism and the energizable rod member, the rod-drive assembly configured to urge the energizable rod member to move the second longitudinal distance X2 upon movement of the deployment mechanism from the first position to the second position.

14. The surgical instrument according to claim 10, further comprising an actuator coupled to the deployment mechanism, the actuator selectively movable from an un-actuated position to an actuated position to move the deployment mechanism from the first position to the second position.

15. The surgical instrument according to claim 14, wherein the actuator includes a lever rotatable about a pivot between the un-actuated position and the actuated position.

16. The surgical instrument according to claim 10, wherein the end effector assembly includes first and second jaw members, at least one of the jaw members movable relative to the other from a spaced-apart position to an approximated position for grasping tissue therebetween, at least one of the jaw members configured to connect to a source or energy for applying energy to tissue grasped therebetween.

17. The surgical instrument according to claim 10, wherein, in the first retracted position, the insulative sleeve member is positioned proximally of the end effector assembly, and wherein, in the first deployed position, the insulative sleeve member is substantially disposed about the end effector assembly.

18. The surgical instrument according to claim 10, wherein, in the second retracted position, the energizable rod member is disposed within the end effector assembly, and wherein, in the second deployed position, at least a portion of the energizable rod member extends distally from the end effector assembly.

19. The surgical instrument according to claim 10, wherein the deployment mechanism is configured to simultaneously move the insulative sleeve member and the energizable rod member the respective first and second longitudinal distances X1 and X2 from their respective retracted positions to their respective deployed positions.

* * * * *